US009731127B2

(12) United States Patent
Kealey et al.

(10) Patent No.: US 9,731,127 B2
(45) Date of Patent: Aug. 15, 2017

(54) MODULATION OF AUTONOMIC NERVOUS SYSTEM ACTIVITY AND INTEGRATED ELECTRODE ASSEMBLIES FOR TRIGEMINAL NEUROSTIMULATION

(71) Applicant: NeuroSigma, Inc., Los Angeles, CA (US)

(72) Inventors: Colin Kealey, Los Angeles, CA (US); Leon Ekchian, Los Angeles, CA (US)

(73) Assignee: NeuroSigma, Inc., Los Angeles, CA (US)

( * ) Notice: Subject to any disclaimer, the term of this patent is extended or adjusted under 35 U.S.C. 154(b) by 0 days.

(21) Appl. No.: 14/907,273

(22) PCT Filed: Apr. 24, 2014

(86) PCT No.: PCT/US2014/035347
§ 371 (c)(1),
(2) Date: Jan. 22, 2016

(87) PCT Pub. No.: WO2014/176450
PCT Pub. Date: Oct. 30, 2014

(65) Prior Publication Data
US 2016/0184585 A1  Jun. 30, 2016

Related U.S. Application Data

(60) Provisional application No. 61/815,718, filed on Apr. 24, 2013.

(51) Int. Cl.
*A61N 1/00* (2006.01)
*A61N 1/36* (2006.01)
(Continued)

(52) U.S. Cl.
CPC ....... *A61N 1/36025* (2013.01); *A61N 1/0456* (2013.01); *A61N 1/0551* (2013.01);
(Continued)

(58) Field of Classification Search
CPC .............. A61N 1/36025; A61N 1/0456; A61N 1/0551; A61N 1/36114; A61N 1/36053; A61N 1/0492
See application file for complete search history.

(56) References Cited

U.S. PATENT DOCUMENTS 6,358,201 B1  3/2002 Childre et al.
8,380,315 B2  2/2013 DeGiorgio et al.
(Continued)

FOREIGN PATENT DOCUMENTS

WO    WO 2012/075192    6/2012

OTHER PUBLICATIONS

International Search Report and Written Opinion, PCT/US2014/035347, Sep. 29, 2014, 11 pages.

*Primary Examiner* — Robert N Wieland
(74) *Attorney, Agent, or Firm* — Haynes and Boone, LLP

(57) ABSTRACT

Cutaneous and subcutaneous TNS embodiments are disclosed for addressing autonomic nervous system imbalances. A cutaneous electrode assembly is applied to a patient's forehead, and a current is pulsed through the electrode assembly to stimulate the supraorbital and supratrochlear nerves on the patient to increase activity for the patient's parasympathetic nervous system. Pulsing the current increases the power spectral density for the patient's heart rate variability in a 0.1 to 0.15 Hz frequency band.

18 Claims, 8 Drawing Sheets

(51) Int. Cl.
*A61N 1/04* (2006.01)
*A61N 1/05* (2006.01)

(52) U.S. Cl.
CPC ..... *A61N 1/36014* (2013.01); *A61N 1/36096* (2013.01); *A61N 1/36107* (2013.01); *A61N 1/36114* (2013.01)

(56) References Cited

U.S. PATENT DOCUMENTS

2008/0058872 A1* 3/2008 Brockway .......... A61B 5/02405
607/2
2008/0132933 A1 6/2008 Gerber
2012/0203301 A1 8/2012 Cameron et al.
2014/0142669 A1* 5/2014 Cook ................... A61N 1/0551
607/116
2014/0330336 A1* 11/2014 Errico ................ A61N 1/36021
607/45
2015/0119898 A1* 4/2015 Desalles .............. A61N 1/0526
606/129

* cited by examiner

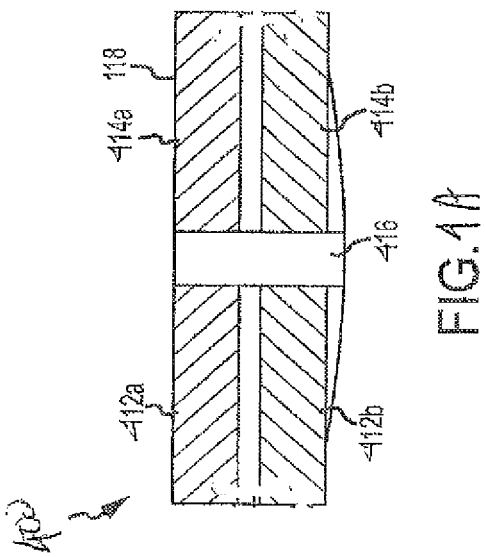

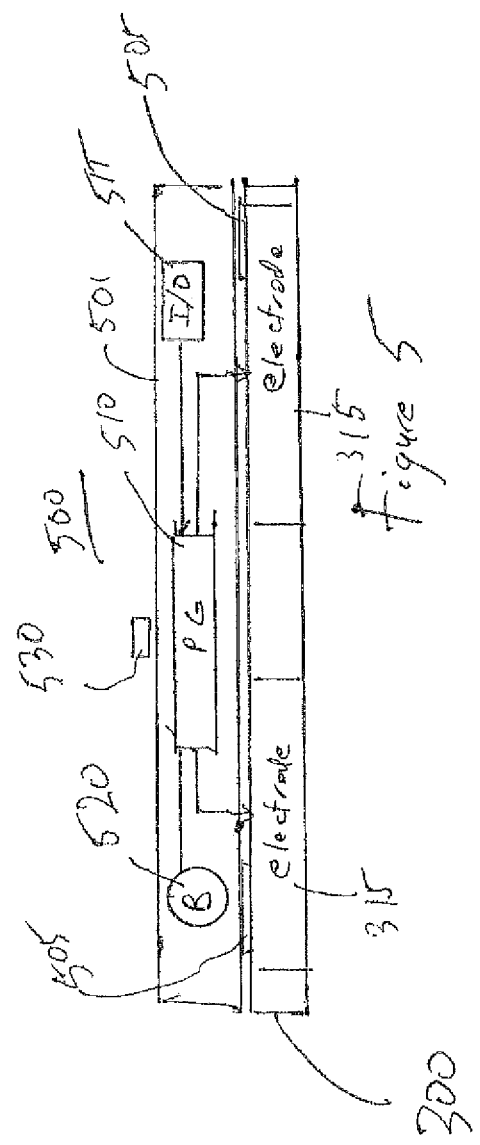

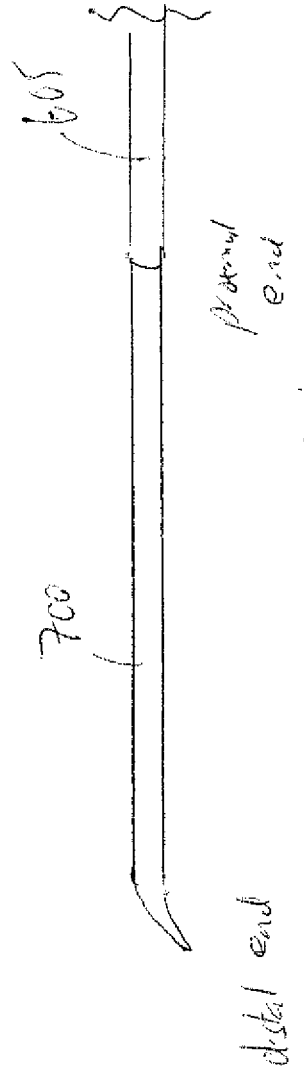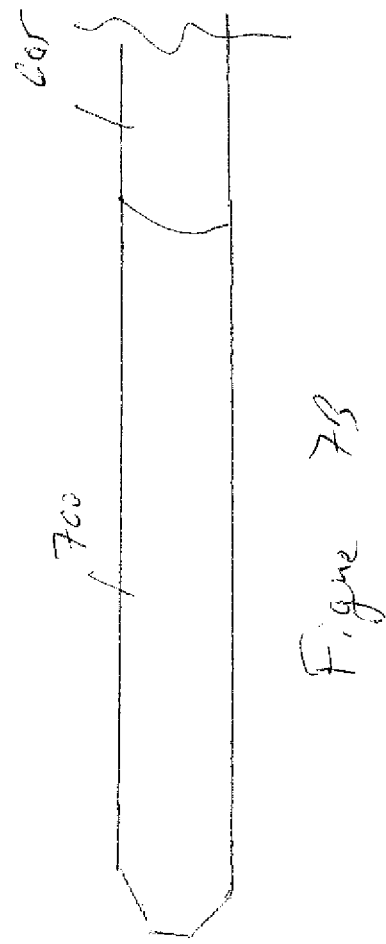

MODULATION OF AUTONOMIC NERVOUS SYSTEM ACTIVITY AND INTEGRATED ELECTRODE ASSEMBLIES FOR TRIGEMINAL NEUROSTIMULATION

RELATED APPLICATIONS

This application is a U.S. national stage application under 35 U.S.C. §371 of International Patent Application No. PCT/US2014/035347, which claims the benefit of U.S. Provisional Application No. 61/815,718, filed Apr. 24, 2013, the contents of which are hereby incorporated by reference in their entirety.

TECHNICAL FIELD

The present disclosure relates to neurostimulation, and more specifically to the stimulation of cranial nerves to modulate autonomic nervous system activity. In addition, the present disclosure relates to an integrated cutaneous electrode assembly for neurostimulation of the trigeminal nerve.

BACKGROUND

The peripheral nervous system comprises pairs of cord-like nerves arising from the brain and the spinal cord and includes both a somatic portion and an autonomic portion. In contrast to the somatic portion, the autonomic portion of the peripheral nervous system is not subject to direct voluntary control. It is the autonomic nervous system that controls functions such as digestion, heart rate, and respiratory rate. To provide this control, the autonomic nervous system (ANS) is in turn composed of the sympathetic and parasympathetic nervous systems. These two systems are thought to act somewhat in opposition to each other. The sympathetic nervous system controls "fight or flight" reflexes whereas the parasympathetic system controls "rest and digest" functions. While this is most certainly an over-simplification, there is no doubt that these two components of the ANS have different functions and exert control over a wide range of organ systems that operate below the level of conscious control. Furthermore, imbalances of the autonomic nervous system have been associated with a wide range of disease states. The best characterized of these is cardiac autonomic dysfunction, which is characterized by increased activity of sympathetic nervous system activity and decreased activity of the parasympathetic nervous system.

A large body of evidence has conclusively demonstrated that patients with congestive heart failure (CHF) have decreased activity of the parasympathetic nervous system and that these changes have been observed following acute myocardial infarction, and in patients with ischemic heart disease. Indeed, loss of parasympathetic nervous system activity is an independent predictor of sudden death, development of lethal cardiac arrhythmias and the likelihood of adverse cardiac events. In addition to its role in cardiac disease, imbalances of the ANS have been associated with a number of other disorders including the metabolic syndrome, Type 1 and 2 diabetes, autoimmune disorders, and anxiety disorders (such as post-traumatic stress disorder or PTSD).

To address imbalance within the ANS, neuromodulation of the vagus nerve has been used. The vagus nerve, like most other cranial nerves, arises in pairs from the brain stem. The vagus nerve includes some somatic fibers for controlling speech but is largely a parasympathetic nerve that enervates assorted organs and muscles including the heart. The parasympathetic control of the heart through the vagus nerve slows the heart rate whereas sympathetic control increases the heart rate. Given this relationship between the vagus nerves and heart rate, various approaches have been developed to electrically stimulate one or both of the vagus nerves to decrease heart rate. But the vagus nerve arises from the brain stem and passes through the carotid sheath in the neck before enervating the viscera in the chest cavity and abdomen. It is thus not readily stimulated using transcutaneous electrodes but instead requires electrode implantation. An implantation on the vagus nerve is inherently quite invasive given the relatively inaccessible location of the vagus nerve. Thus, electrode implantations for vagus nerve stimulation have assorted health risks and dangers. But the need for neurostimulation to balance ANS activity is well known with regard to cardiac health.

Accordingly, there is a need in the art for less invasive neurostimulation techniques for balancing ANS activity.

BRIEF DESCRIPTION OF THE DRAWINGS

The present disclosure, both as to its organization and manner of operation, may be understood by reference to the following description, taken in connection with the accompanying drawings, in which:

FIG. 7A is a side view of a dissection tool and an engaged electrode lead.

FIG. 7B is a plan view of the dissection tool and engaged electrode lead of FIG. 7A.

DETAILED DESCRIPTION

Figures 1A, 1B:
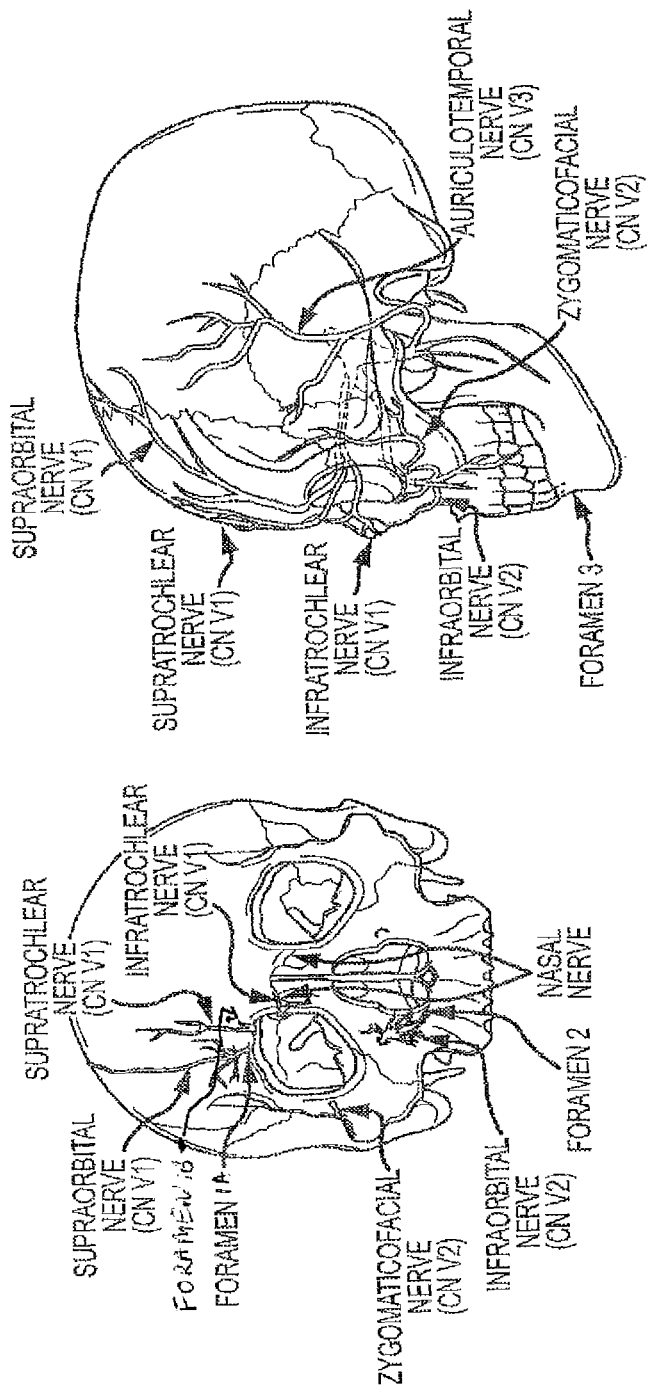
FIGS. 1A and 1B illustrate the location of several branches (nerves) of the trigeminal nerve and the location of the major foramina for the superficial branches of the trigeminal nerve.

To satisfy the need in the art for improved and less invasive ANS neurostimulation approaches, trigeminal nerve stimulation (TNS) techniques are disclosed. TNS is quite advantageous in that it has the same or greater efficacy than prior art vagus nerve neurostimulation techniques but is much less invasive and thus far safer. A number of proxies may be used to measure or quantify the ANS modulation provided by the TNS techniques disclosed herein. For example, with regard to ANS activity, Heart Rate Variability (HRV) is a widely accepted proxy. Broadly speaking, HRV is a measurement of the beat-to-beat change in heart rate and is assessed via a variety of methods. In healthy patients, the time duration between heart beats varies. In contrast, cardiac-compromised patients have less variability between beats. Indeed, reduced HRV is a known predictor of mortality for patients with myocardial infarctions. To determine the HRV, the time domain behavior for the heart rate is transformed into the frequency domain using techniques such as the Fourier transform. For example, spectral analysis techniques may be applied to the HRV time domain waveform to discern the power spectral density (PSD) of the frequency domain representation of the HRV. Using the PSD, the relative contributions of the sympathetic and parasympathetic divisions of the ANS may be determined. The HRV PSD is divided into three frequency bands including a low frequency (LF) band (0.04 to 0.15 Hz) and a high frequency (HF) band (0.15 to 0.4 Hz). The HF band is a measurement of parasympathetic nervous system activity whereas the LF band measures both sympathetic and parasympathetic activity. It is believed that the sympathetic nervous system contributes very little above the 0.1 Hz frequency spectrum. Thus the region of the HRV frequency spectrum in the 0.1 Hz domain represents a middle-ground between the sympathetic and parasympathetic branches of the ANS.

As will be discussed further herein, TNS is shown to markedly increase the HF band power component in the HRV PSD. This is quite advantageous as TNS increases HRV in a non-invasive or minimally-invasive technique. The TNS techniques disclosed herein use electrodes that have been developed for the treatment of neurological and neuropsychiatric disorders for both transcutaneous and subcutaneous applications. Transcutaneous embodiments will be discussed first followed by a discussion of subcutaneous embodiments.

Transcutaneous Embodiments

In the least invasive form of TNS, a cutaneous electrode assembly is applied to the forehead to stimulate the ophthalmic nerves. The electrode assembly extends longitudinally from at least a first electrode contact and across a central insulating to at least a second electrode contact. Such a longitudinal extent is quite advantageous in that a lay person can readily center an electrode assembly on their forehead adjacent to or above their eyebrows. In some embodiments, the electrode assembly may include an alignment feature such as a centrally-located angular point that a lay person may also easily align with their nasal midline. The central insulating region is sized such that, with the electrode assembly centered on the forehead, the first electrode contact overlays the supratrochlear nerve and/or the supraorbital nerve arising from a first orbital arch and such that the second electrode contact overlays the supraorbital nerve and/or the supratrochlear nerve arising from a remaining second orbital arch. Thus, a lay person can position and apply the cutaneous electrode assembly so that the ophthalmic nerves are electrically stimulated by the corresponding electrode contacts without requiring any specialized training or anatomical knowledge. Moreover, because the ophthalmic nerves on the forehead are relatively shallow with regard to the skin surface, they are readily stimulated by cutaneous electrodes at current levels that are easily tolerated by patients. The amount of current may thus be regulated so that the brain itself is never subjected to any current (or subjected to vanishingly-small amounts of current that have no deleterious effects). A cutaneous electrode application to the forehead thus involves none of the risks involved with the conventional invasive approaches and also isolates the brain from exposure to electrical current.

The cutaneous electrode assembly may be applied for acute or prolonged treatment. In one embodiment, the electrode assembly may be applied during sleeping hours. The electrode assembly can then be removed upon waking so that a patient can resume a normal routine during the daytime hours. To better appreciate the features of the TNS techniques discussed herein, a brief review of the trigeminal nerve and the subcutaneous and connective tissue of the human head that overlies the trigeminal nerve is now provided. With reference to FIGS. 1A and 1B, the trigeminal nerve is the largest cranial nerve and has extensive connections with the brainstem and other brain structures. The trigeminal nerve, also named the fifth cranial nerve or "CN V," has three major sensory branches over the face, all of which are bilateral, and highly accessible. The ophthalmic nerve is frequently referred to as the $V_1$ division and includes the supraorbital and supratrochlear nerves that supply sensory information about pain, temperature, and light touch to the skin of the forehead, the upper eyelid, the anterior part of the nose, and the eye. The $V_2$ division includes the infraorbital and maxillary nerves. The infraorbital branch supplies sensory information about pain, temperature, and light touch sensation to the lower eyelid, cheek, and upper lip. Finally, the $V_3$ division includes the auriculotemporal, lingual, and inferior alveolar branches of the mandibular nerves. The inferior alveolar branch supplies similar sensory modalities to the skin of the lower face (e.g. jaw and tongue) and lips.

These branches exit the skull through three groups of foramina or notches, as shown in FIGS. 1A and 1B. The supraorbital and supratrochlear nerves exit at foramina 1. In particular, the foramen (or notch) for the supratrochlear nerve is approximately 2.1-2.6 cm from the nasal midline (in adults), and is located immediately above the orbital ridge that is located below the eyebrow. The supratrochlear foramen is indicated as foramen 1B. In contrast, the foramen (or notch) for the supraorbital nerve is located more laterally from the nasal midline: e.g., approximately 3.2 cm from the nasal midline in adults. This foramen is indicated as foramen 1A. The infraorbital branch or maxillary nerve exits at foramen 2, approximately 2.4-3.0 cm from the nasal midline (in adults) and the mentalis nerve exits at foramen 3, approximately 2.0-2.3 cm from the nasal midline (in adults). Other sensory branches, including the zygomaticofacial, zygomaticoorbital, zygomaticotemporal, and auriculotemporal, arise from other foramina.

Fibers from the three major branches join together to form the trigeminal ganglion. From there, fibers ascend into the brainstem at the level of the pons to synapse with the main sensory nucleus of the pons, the mesencephalic nucleus of V, and the spinal nucleus and tract of V. Pain fibers descend in the spinal nucleus and tract of V, and then ascend to the ventral posterior medial nucleus (VPM) of the thalamus, and then project to the cerebral cortex. Light touch sensory fibers are large myelinated fibers, which ascend to the ventral posterior lateral (VPL) nucleus of the thalamus, and also project to the cerebral cortex. Afferent sensory fibers project from the trigeminal nuclei to the thalamus and the cerebral cortex.

Figure 2:
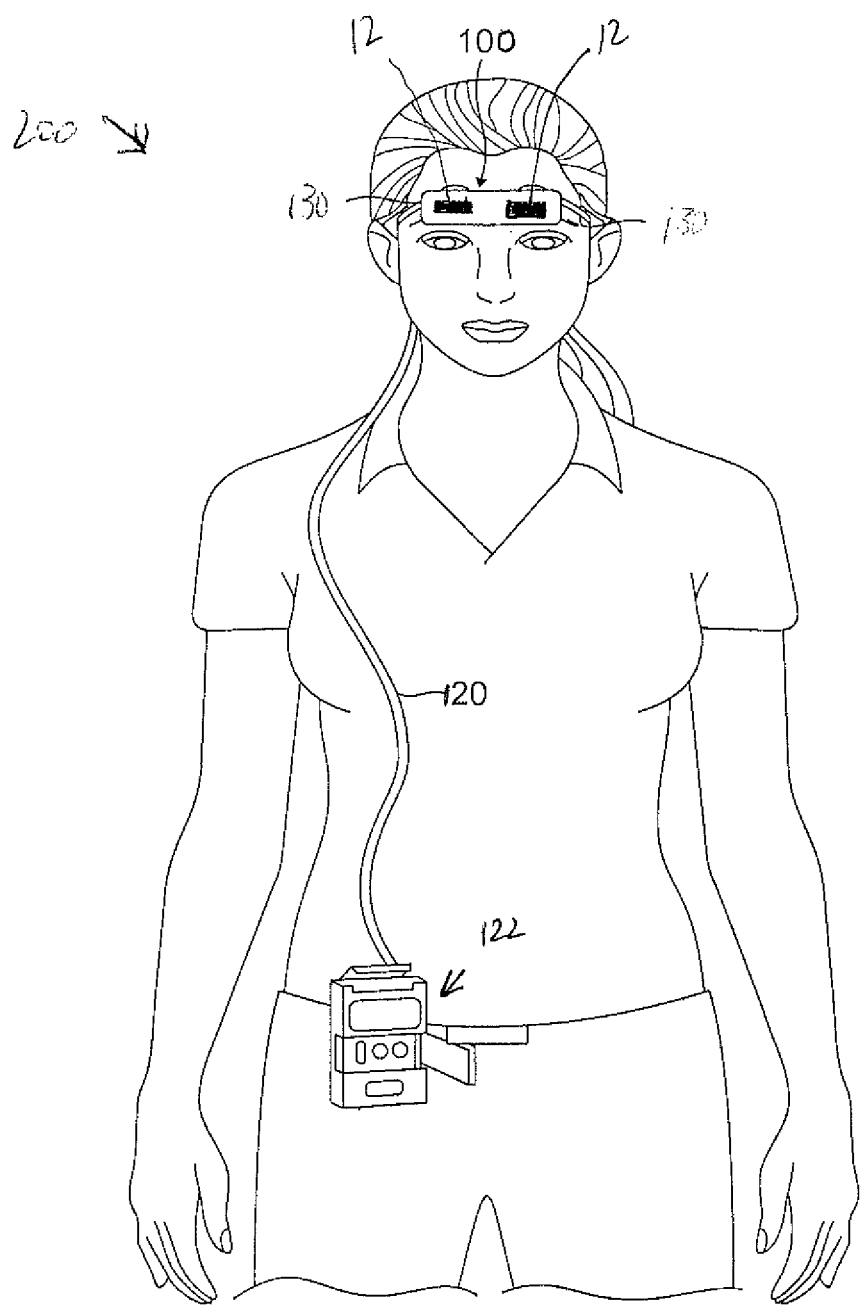
FIG. 2 depicts a patient with a cutaneous electrode system according to aspects of the present disclosure.

With regard to a given supraorbital arch (either the left or right side of the forehead), the corresponding supraorbital nerve and the adjacent supratrochlear nerve are referred to herein as an "ophthalmic nerve pair." In this fashion, the ambiguity that results from referring to just the supraorbital nerve (or the supratrochlear) as the "ophthalmic" nerve is avoided. Given the location of each ophthalmic nerve pair, they are readily stimulated by a cutaneous electrode assembly having electrode contacts 12 such as shown in FIG. 2 for a system 200 including a cutaneous electrode assembly 100, electrical cable or wire 120 and an external neurostimulator or pulse generator 122. In system 200, electrode assembly 100 includes a pair of electrode contacts 12 that are positioned for the bilateral simultaneous stimulation of both ophthalmic nerve pairs. Referring back to the nerve locations as discussed with regard to FIGS. 1A and 1B, note that there is an electrode contact 12 in system 200 over and lateral to each supraorbital nerve. A current driven through one electrode contact 12 will thus pass across not only the supraorbital nerves but also across the supratrochlear nerves. As shown in FIG. 1A, each supraorbital nerve arises from its foramen or notch 1A just medially to the center of each supraorbital ridge. Referring again to FIG. 2, cutaneous TNS excitation is thus readily achieved by lay people in that each electrode assembly 100 is readily centered on the forehead such that each electrode contact 12 is positioned over or adjacent to each supraorbital nerve foramen or notch so as to stimulate the corresponding ophthalmic nerve pair. The width of each electrode contact 12 may be such that it is greater than the expected spacing between the supraorbital nerve and the supratrochlear nerve in a given ophthalmic nerve pair. This is quite advantageous as compared to prior art TNS approaches in which individual contacts were positioned by palpating for the supraorbital notch or foramen and attaching an electrode over or above the foramen. Such an individual contact placement is problematic in that a lay person may not attach the contacts properly, which may result in excessive current exposure such that the brain itself receives appreciable currents. For example, currents tend to penetrate deeper as the electrode spacing is increased. A lay person could thus space individually-placed electrodes too far apart so as to raise the danger of exciting deeper currents that penetrate to the brain. But with electrode assembly 100, the lay person may readily center its midline with the nasal midline. Since the electrode contacts 12 are positioned apart so that each electrode contact 12 stimulates the underlying ophthalmic nerve pair when electrode assembly 100 is centered with regard to the nasal midline, the problems and dangers of prior art individual electrode application are avoided.

The pulse generator 122 is portable and attached to, for example, a belt of the patient. However, either a portable or non-portable pulse generator may be used. In alternative embodiments discussed further below, electrode assembly 100 may be integrated with a pulse generator. In some embodiments, the system 200 may also include a regulation device (not illustrated) to ensure safe use of the system. The regulation device is configured to be attached to or integrated with the pulse generator 122 and is configured to govern the maximum charge balanced output current below approximately 30-50 mA to minimize current penetration to the brain and increase patient tolerance. The regulation device may be internally programmed to range from 0.25-5.0 mA, 0-10 mA, 0-15 mA, depending on the surface area, placement, and orientation of the electrode assembly 100, and whether the electrode assembly 100 is stimulating near or adjacent to the skull, or away from the skull, where current ranges may be higher or lower. In contrast, conventional TENS units stimulate with maximum output currents of up to 100 mA, which result in currents which may penetrate the skull and which may not be well tolerated.

In some embodiments, the electrode assembly 100 further includes a retainer element 130 configured to secure the electrode assembly to a patient's forehead. In one embodiment, the retainer element 130 can be an elastic band or strap that encircles the back of the head to secure electrode assembly 100 to the patient. In alternative embodiments, the electrode assembly 100 can be secured in place by a hat or a cap which also serves to conceal the electrode assembly 100 from view. In still other embodiments, the electrode assembly 100 may be secured by adhesive, such as an adhesive strip, an adhesive backing surrounding the conducting area or an adhesive conductive gel.

Figure 3A:
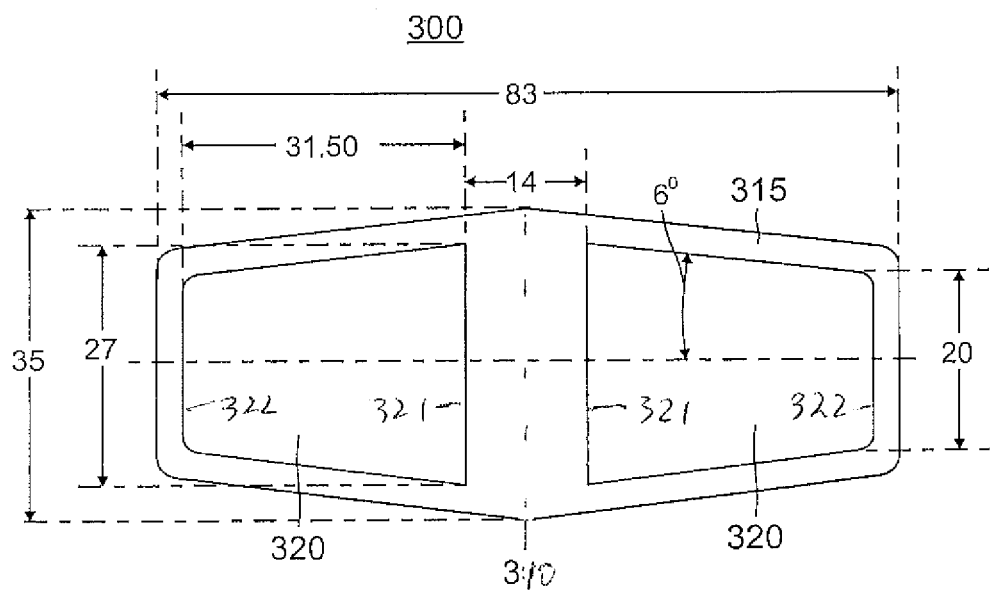
FIG. 3 is a plan view of a cutaneous electrode assembly that includes a pair of contacts configured to stimulate both ophthalmic nerve pairs.

Referring now to FIG. 3A, an example electrode assembly 300 includes a pair of electrode contacts 320 received in apertures within an adhesive-covered foam layer 315. For example, foam layer 315 may comprise a medical grade foam layer and electrode contacts 320 may comprise a conductive hydrogel electrically driven by an electrode pad (not illustrated). To assist in the alignment of electrode assembly 300 with the nasal midline, a midline alignment feature such as a convex angle 310 (e.g., an angle of 168 degrees) may be defined by the bottom and top edges of foam layer 315. Alternatively, only one of the bottom or top edges of foam layer 315 may include such an alignment feature. Gel pads 320 are separated by a central insulating region that may be 14 mm wide. Given the chevron shaping resulting from convex angles 315, each electrode contact/gel pad 320 narrows by 12 degrees from a medial edge 321 that may be 27 mm wide to a lateral edge 322 that may be 20 mm wide. Each gel pad 320 may have a longitudinal extent of 31.5 mm. The lateral edge 322 of each gel pad 320 is thus 38.5 mm from the nasal midline. Such a pad spacing assures that each gel pad 320 is positioned to stimulate both the supraorbital nerve and the supraorbital nerve in an ophthalmic nerve pair for the vast bulk of the adult population. But some adults will require even a greater pad width such as 34 mm to assure that the supraorbital nerves receive adequate stimulation.

Figure 3B:
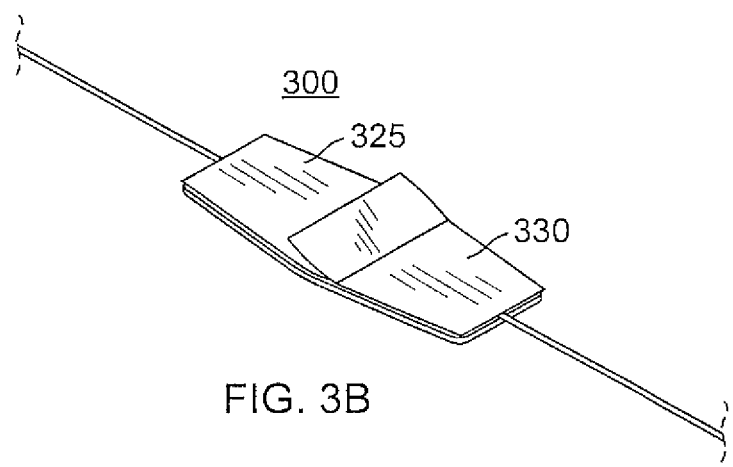

An additional foam layer (not illustrated) serves as a back wall to the apertures in foam layer 315 that receive gel pads 320. Prior to application, gel pads 320 and the adhesive surface of foam layer 315 are protected by, for example, by wax by waxed paper flaps 330 and 325 as shown in FIG. 3B. Flaps 330 and 325 function in the familiar "band aid" fashion such that each flap includes a projecting end that a user may readily pull on to release the corresponding flap from windowed electrode assembly 300. With the gel pads 320 and the adhesive surface then uncovered, the patient may proceed to adhere electrode assembly 300 to their forehead as discussed with regard to FIG. 2.

Additional contacts may be located along each nerve fiber. In this fashion, a pair of contacts on a given nerve fiber may be stimulated such that the current between the pair of contacts is driven in an afferent fashion (towards the trigeminal ganglion). For example, an electrode assembly 400 of FIG. 4A includes a first pair of electrode contacts 412a, 412b for placement above the supraorbital ridge at one side of the forehead, and a second pair of electrode contacts 414a, 414b for placement above the supraorbital ridge on an opposing side of the forehead of a patient. The first and second contact pairs are insulated from other by an insulating region 416. The electrode assembly 400 comprises an inner contact surface 418 that comes into contact with a patient's skin at four contact areas, each corresponding to one of the four electrode contacts 412a, 412b, 414a, 414b. The inner contact surface 418 comprising the four contact areas includes a buffered gel-like adhesive that provides good electrical conductivity with minimum skin irritation, an example of such gel includes the commercially available hydrogels from AmGel Technologies (AmGel Technologies, Fallbrook, Calif., USA). Each electrode contact 412a, 412b, 414a, and 414b has a width equal to or greater than the expected separation between a supraorbital nerve and the adjacent supratrochlear nerve in an ophthalmic nerve pair.

The electrode assembly 400 may be configured to stimulate both the right and left ophthalmic nerve pairs either simultaneously or asynchronously. The insulative connection region 416 serves to assist a patient in lining up the electrode assembly 400 with the midline of the nose to ensure proper placement of the electrode assembly 400 over both ophthalmic nerve pairs. The supratrochlear foramen (or notch) will typically be located about 2.1 to 2.6 cm from the nasal midline of an adult patient. Similarly, the supraorbital foramen (or notch) will typically be located about 3.2 cm from the nasal midline of an adult patient. The nerve fibers will tend to rise in a parallel fashion from notches. In other words, if a contact has a width sufficient to overlay the foramina for an ophthalmic nerve pair, that same contact would also overlay the corresponding ophthalmic nerve pair fibers if moved further up the forehead toward the hairline. Each contact should thus have a width and a positioning such that both nerves in the corresponding ophthalmic nerve pair are stimulated. By aligning region 416 with the nasal midline, a patient may readily position the electrode assembly 400 on the forehead without knowledge of the location of the ophthalmic nerve pairs or their foramina, thereby reducing the possibility of inadequate stimulation due to errors in positioning of the contacts.

Figure 4B:
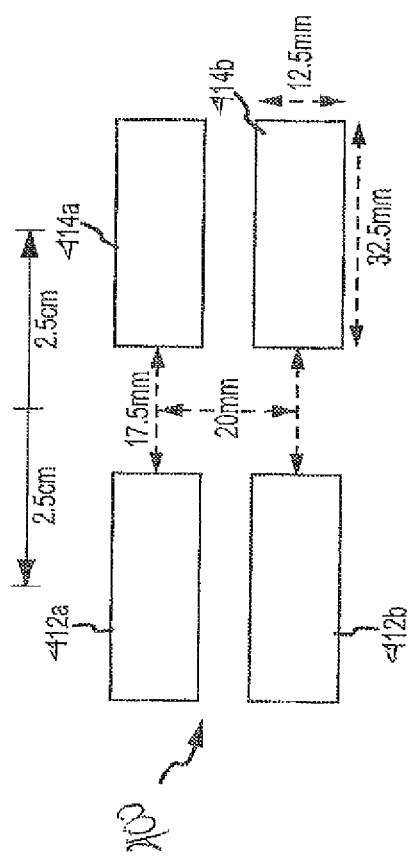
FIG. 4B illustrates the dimensions for the two pairs of contacts of FIG. 4A in one embodiment.

The placement of the first contact pair 412a, 412b and the second contact pair 414a, 414b on opposite sides of the nasal midline assures that stimulation current moves in the afferent (or efferent) direction. Example dimensions for the contacts are shown in FIG. 4B. In this embodiment, the mid-point of each of the contacts is approximately 2.5 cm (in other embodiments, such a mid-point may range from 1.5 cm to 3.5 cm) from the nasal midline. The electrode size and the inter-electrode distance may vary for children and adults, males and females based on anatomical differences. Each contact is approximately 32.5 mm in width by 12.5 mm in height and the distance between, for example, the upper pair of contacts 412a and 414a is 17.5 mm. The separation between each contact pair (e.g. between upper contact 412a and the lower contact 412b is 20 mm. It is simpler, however, to direct the current neither in an afferent nor in an efferent fashion but instead orthogonally across the fibers using just a single pair of contacts as discussed with regard to FIGS. 2A and 2B.

Regardless of whether a single pair of contacts are used to stimulate both ophthalmic nerve pairs or whether each ophthalmic nerve pair is stimulated by its own pair of contacts, the current maybe pulsed at a stimulus frequency between about 20 Hz and about 300 Hz, at a pulse duration between 50 microseconds (μsec) and 250 μsec, at an output current density of less than 25 mA/cm2 and an output charge density of less than 10 μCoulomb/cm2 at the cerebral cortex for at least one-half to one hour per day. The pulsing may be performed in a duty cycle of 30 seconds of pulsing following by 30 seconds of rest.

In various embodiments, the stimulation is delivered at a specific pulse width or range of pulse widths (or pulse duration). The stimulation can be set to deliver pulse widths in any range within a lower limit of about 10 microseconds and an upper limit of about 3 seconds. In various embodiments, the stimulation can be set to deliver pulse widths in the range greater than and/or less than one or more of 50 μs, 60 μs, 70 μs, 80 μs, 90 μs, 100 μs, 125 μs, 150 μs, 175 μs, 200 μs, 225 μs, 250 μs, up to 500 μs. Those of skill in the art will recognized that one or more of the above times can be used as a border of a range of pulse widths.

In some embodiments, the stimulation amplitude is delivered as a voltage or current controlled stimulation. In other embodiments it can be delivered as a capacitive discharge. In various embodiments, the current amplitude can be in any range within a lower limit of about 300 μA and an upper limit of about 30 mA-35 mA, depending on the surface area of the electrodes, inter-electrode distance, the branch(es) stimulated, and the modeling data as described above. In various embodiments, the amplitude can be in a range greater than and/or less than one or more of 50 μA, 75 μA, 100 μA, 125 μA, 150 μA, 175 μA, 200 μA, 225 μA, 250 μA, 275 μA, 300 μA, 325 μA, 350 μA, 375 μA, 400 μA, 425 μA, 450 μA, 475 μA, 500 μA, 525 μA, 550 μA, 575 μA, 600 μA, 625 μA, 650 μA, 675 μA, 700 μA, 725 μA, 850 μA, 875 μA, 900 μA, 925 μA, 950 μA, 975 μA, 1 mA, 2 mA, 3 mA, 4 mA, 5 mA, 6 mA, 7 mA, 8 mA, 9 mA, 10 mA, 11 mA, 12 mA, 13 mA, 14 mA, 15 mA, 16 mA, 17 mA, 18 mA, 19 mA and 20 mA. Those of skill in the art will recognize that one or more of the above amplitudes can be used as a border of a range of amplitudes.

In various embodiments, the stimulation can be delivered at one or more frequencies, or within a range of frequencies. The stimulation can be set to be delivered at frequencies in any range within an upper limit of about 500 Hz and a lower limit of about 10 Hz. In various embodiments, the stimulation can be set to be delivered at frequencies less than, and/or greater than one or more of 50 Hz, 45 Hz, 40 Hz, 35 Hz, 30 Hz, 25 Hz, 20 Hz, 15 Hz, or 10 Hz. In various embodiments, the stimulation can be set to be delivered at frequencies greater than, and/or less than, one or more of 20 Hz, 30 Hz, 40 Hz, 50 Hz, 60 Hz, 70 Hz, 80 Hz, 90 Hz, 100 Hz, 125 Hz, 150 Hz, up to 300 Hz. Those of skill in the art will recognize that one or more of the above frequencies can be used as a border of a range of frequencies.

In various embodiments, the stimulation is delivered at a specific duty cycle or range of duty cycles within a range from 100% down to about 5%. The duty cycle is defined with regard to a duty cycle period. In each duty cycle period, the current is pulsed during an on portion of the duty cycle period and not pulsed during a remaining off portion of each duty cycle period. The ratio of the on portion to the duty cycle period defines the duty cycle. For example, if the on portion is one half of the duty cycle period, the duty cycle would be 50%. In various embodiments, the stimulation can be set to be delivered at a duty cycle in the range greater than and/or less than one or more of 5%, 10%, 15%, 20%, 25%, 30%, 35%, 40%, 45%, 50%, 55%, 60%, 65%, 70%, 75%, 80%, 85%, 90%, 95%, or 100%. The period used to define the duty cycle may be 60 seconds such that a 50% duty cycle would comprise 30 seconds of pulsing and 30 seconds of quiescence in each duty cycle period. In some embodiments, to ensure preservation of the nerve, a duty cycle of 10% to 50% may be preferable. In some embodiments, duty cycles up to 100% may be useful in particular circumstances. Those of skill in the art will recognize that one or more of the above percentages can be used as a border of a range of duty cycles.

Clinical Results for a Transcutaneous Embodiment

A clinical study of the physiologic effects of TNS has demonstrated dramatic changes in HRV using the electrode assembly 300 of FIGS. 3A and 3B. But it will be appreciated that similar clinical results are expected for the alternative transcutaneous electrode assemblies discussed herein. In this study, subjects were first asked to sit quietly for a period of 5 minutes so that a baseline PSD in the 0.1 to 0.15 Hz band could be obtained. A 5 minute application of bilateral transcutaneous TNS was then applied, whereupon the PSD in the 0.1 to 0.15 Hz band was again obtained. For demonstration purposes, the duty cycle was continuous for a 120 Hz pulse rate and a biphasic pulse width of 250 µs. To set the current rate, the patients adjusted the current to a tolerable yet stimulating level such as 4 to 8 milliamps. Given this stimulation, four subjects provide the following results: A mean PSD in the 0.1 to 0.15 Hz band with no TNS was 50.5 with a standard deviation of 14.2. But this same mean PSD increased to 77.75 after the five minute application of TNS with a standard deviation of 12.8. Accordingly, TNS dramatically increased HRV with such a brief and acute application of TNS.

The implication of these findings is profound in that a large number of disease states are associated with decreased activity of the parasympathetic nervous system. Therefore the ANS regulating effects of TNS may treat a wide-range of conditions involving ANS imbalance including congestive heart failure, acute cardiac arrhythmias, ischemic heart disease, metabolic syndrome, Type 1 & 2 diabetes, Sjogren's syndrome, erectile dysfunction, ADHD, PTSD, and autoimmune disorders (e.g. rheumatoid arthritis, psoriatic arthritis, spondylitis, systemic lupus erythematosus, irritable bowel syndrome, Crohn's disease, ulcerative colitis, and inflammatory bowel disease). In other embodiments, different values of the operational parameters may be used. In one embodiment, the values of the operational parameters are selected such that a patient will experience a stimulation sensation, such as a mild tingling over the forehead and scalp without being in discomfort or in pain. The neurostimulation parameters are important factors in the treatment method. In one embodiment, the values of the operational parameters are selected to minimize skin irritation, burns, undesired effects on the brain and/or the ophthalmic nerves. In another embodiment, the method of selecting operational parameters comprises evaluating variables such as the configuration and size of the electrode, the pulse duration, the electrode current, the duty cycle and the stimulation frequency, each of which are important factors in ensuring that the total charge, the charge density, and charge per phase are well within accepted safety limits for the skin, nerve and brain. For example, to minimize skin irritation, it is not sufficient to merely consider the total current, but the current density needs to be defined. Additionally, it is important to select the electrical stimulation parameters, electrode design, and inter-electrode distance, such that the electrical stimulation zone includes the ophthalmic nerve (approximately 3-4 mm deep), or other target nerve, while preventing or minimizing current penetration beneath the skull bone.

An Integrated Electrode Assembly

Although a cutaneous neurostimulation of the ophthalmic nerve pairs is advantageous for balancing ANS activity as compared to an invasive implantations on, for example, the vagus nerve, a patient may object to the wires or cable necessary to drive the electrodes from the pulse generator. The following integrated electrode embodiments eliminate wires as the pulse generator is itself integrated with the electrode assembly.

A cutaneous electrode assembly is typically replaced at regular intervals. For example, if a patient only applies the electrode assembly at night, each application would typically involve the use of a new electrode assembly that would then be discarded the next day. It would of course be expensive to also discard the pulse generator. Thus, the pulse generator is removably attached to the integrated electrode assembly disclosed herein such that the patient or clinician can reapply it to another electrode assembly upon the discarding of a used electrode assembly. For example, an adhesive tape layer or Velcro may be used for such a removable attachment. Alternatively, the pulse generator may be coupled to the electrode assembly through mechanically-actuated clips.

The pulse generator would include an integrated battery so that no wires are necessary to power the integrated electrode assembly. This battery may be rechargeable or replaceable as necessary. To keep costs low, the pulse generator may include only an off and on switch. Operating parameters such as the pulse repetition rate, pulse width, duty cycle, and current may be fixed or may be adjustable through a wireless interface. For example, the pulse generator may include a WiFi or Bluetooth wireless interface. A remote control unit would then wirelessly interface through the pulse generator's wireless interface to control operating parameters.

Figure 5:
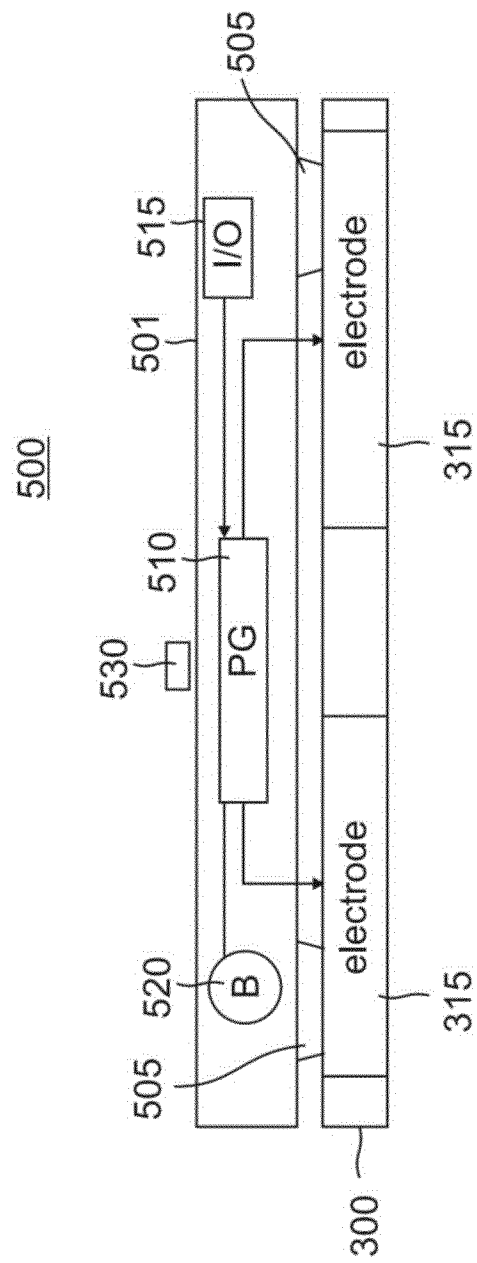
FIG. 5 is a cross-sectional view of an integrated electrode assembly.
Figure 6:
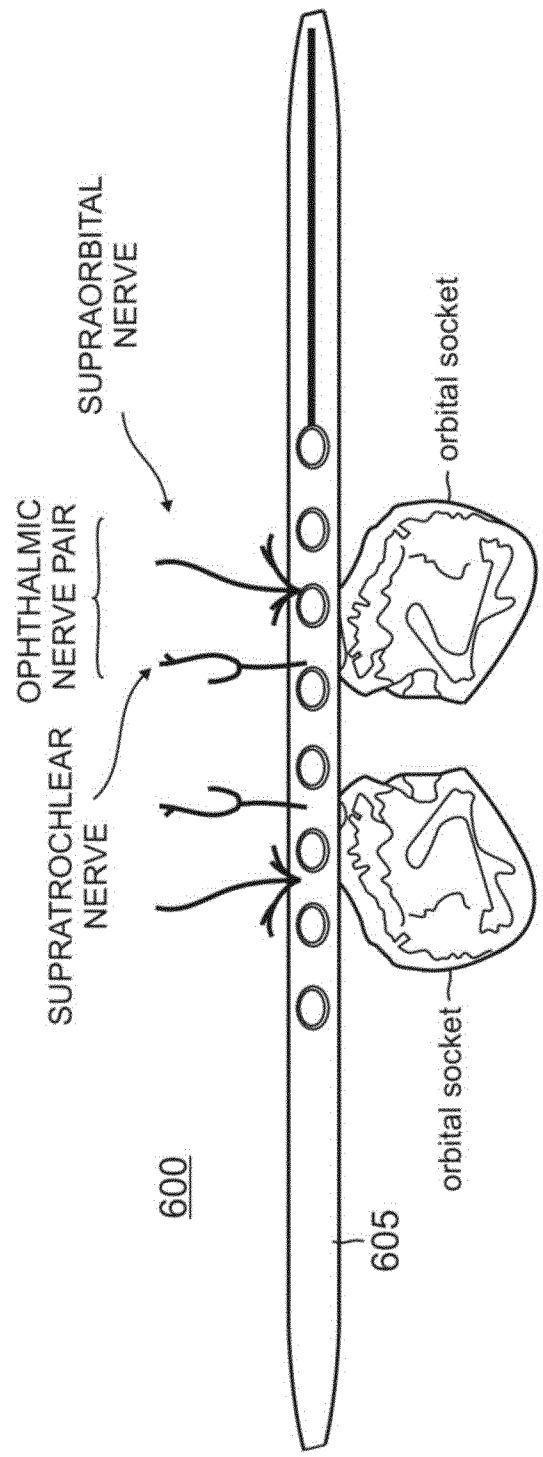

An example embodiment for an integrated electrode assembly 500 is shown in FIG. 5. Integrated electrode assembly 500 includes an electrode assembly such as electrode assembly 300 as discussed with regard to FIGS. 3A and 3B. A housing 501 is removably attached to electrode assembly 300 through, for example, adhesive tape patches 505. In other embodiments, Velcro patches (not illustrated) may be used to removably attach housing 501 to electrode assembly 300. Housing 501 includes a pulse generator 510 that may be configured through a wireless interface (I/O) 515 to set the pulse repetition frequency and other operating parameters as discussed above. Pulse generator 510 drives electrode contacts 315 according the operating parameters set by I/O interface 515 in electrode assembly 300 to provide neurostimulation. A battery 520 provides power to pulse generator 510 so that integrated electrode assembly 500 is wireless and self contained. A switch 530 enables a user to turn pulse generator 510 on and off. In other embodiments, I/O interface 515 is manually configured by the user as opposed to being configured wirelessly to set the operating parameters for pulse generator 510.

In one embodiment, a patient would first connect the housing 501 and electrode assembly 300 by peeling away a single or a plurality of plastic liners from adhesive tape patches 505. In an alternative embodiment, the patient would first connect housing 501 and electrode assembly 300 by snapping together mechanical connectors built into housing 501 and electrode assembly 300 to ensure proper electric contact between pulse generator 510 and electrodes 315. The patient would then peel away a single or a plurality of plastic liners or waxed flaps from an adhesive skin-facing surface of electrode assembly 300 for attachment to the forehead as discussed with regard to FIG. 2.

It is preferable that electrode assembly 300 and housing 501 be as low in profile and weight as possible for the comfort of the patient, yet providing sufficient battery capacity to avoid having to replace or recharge more than once during a 24 hour period.

Electrode assembly 300 may be flexible whereas housing 501 may be rigid or flexible. In a rigid embodiment, housing 501 may be contoured to the expected curvature across the orbital arches. Alternatively, housing 501 may employ flex circuits and flexible thin film batteries to allow for sufficient flexibility so as to flexibly contour to the forehead. In addition to switch 530, housing 501 may be equipped with a small display and a plurality of keys such as an ON/OFF key and up and down keys to control multiple functions such as the selection of stimulation parameters like current, frequency and pulse width. The keys may include a SET key as well as a LOCK key to prevent inadvertent changes to the set parameters.

Battery 520 may comprise a high density rechargeable lithium-ion or lithium-polymer batteries. If flexible batteries are required, rechargeable thin-film solid state batteries could be employed. High density thin-profile batteries minimize the volume of the housing 501, which would otherwise need to be bulkier so as to house larger profile batteries. The battery (or batteries) 520 could be stored in a separate compartment in housing 501 and be replaced as necessary. Alternatively, the entire pulse generator/battery unit could be sealed such that it would be discarded when the battery 520 needs to be replaced, similar to implantable neuromodulation devices.

Electrical coupling between pulse generator 510 and electrodes 315 may be accomplished through male/female couplers (not illustrated). Alternatively, housing 510 may include conductive patches on its electrode-assembly-facing surface. Referring back to FIG. 3A, the conductive gel pads that form electrodes 315 may be held within foam layer 315 such that the gel pads are exposed on both the skin-facing and the housing-facing surfaces of electrode assembly 300. In other words, the apertures in foam layer 305 would not only be open on the skin-facing surface but would also be open on the housing-facing surface of electrode assembly 300. To hold the gel pads more securely in backing layer 305, the apertures would be partially closed on the housing-facing surface. In contrast, the skin-facing aperture is larger to accommodate the ophthalmic nerve spacing discussed above such that both the supraorbital and the supratrochlear nerve in an ophthalmic nerve pair are adequately stimulated. Such an embodiment is advantageous in that the construction of electrode assembly 300 is simplified in that no wires or electrical couplers are necessary to electrically couple to the conductive patches on the electrode-assembly-facing surface of housing 501.

It will be appreciated that an integrated electrode assembly such as assembly 500 is not limited to just the modulation of the autonomic nervous activity by may also be used for treatment of a wide variety of neurological and neuropsychiatric disorders as well as medical disorders that do not involve ANS imbalances but do respond to TNS modulation.

Subcutaneous Embodiments

The neurostimulation of the ophthalmic nerve pairs for modulating autonomic nervous activity is not limited to cutaneous embodiments. In other embodiments, the electrode assembly may be a subcutaneous electrode assembly such as discussed in U.S. application Ser. No. 12/898,696, the contents of which are incorporated by reference herein. A particularly advantageous subcutaneous electrode and implantation technique will now be discussed. To provide a better appreciation for the advantageous features of this technique, the scalp anatomy will first be reviewed. The scalp comprises a number of layers that include a loose areolar connective tissue layer. In industrial accidents in which the scalp is avulsed from the skull such as when sufficient locks of hair are caught in machinery, it is the loose areolar connective tissue that is divided during the avulsion. On the forehead above the supraorbital ridge, the loose areolar connective tissue is covered by the frontalis muscle. The technique disclosed herein exploits the loose areolar connective tissue using a blunt dissection tool that will naturally follow the plane defined by the loose areolar connective tissue as opposed to dissecting into the tougher frontalis muscle or the much tougher underlying pericranium. Once inserted into the plane defined by the areolar connective tissue, the dissection tool may be displaced across the forehead from an insertion point to an extraction point. A subcutaneous electrode attaches to a proximal portion or end of the dissection tool such that as the dissection tool is displaced across the forehead and removed from the extraction point, the subcutaneous electrode is pulled through the plane defined by the areolar connective tissue. In this fashion, the subcutaneous electrode may be pulled to suitable attachment position.

Figure 6:
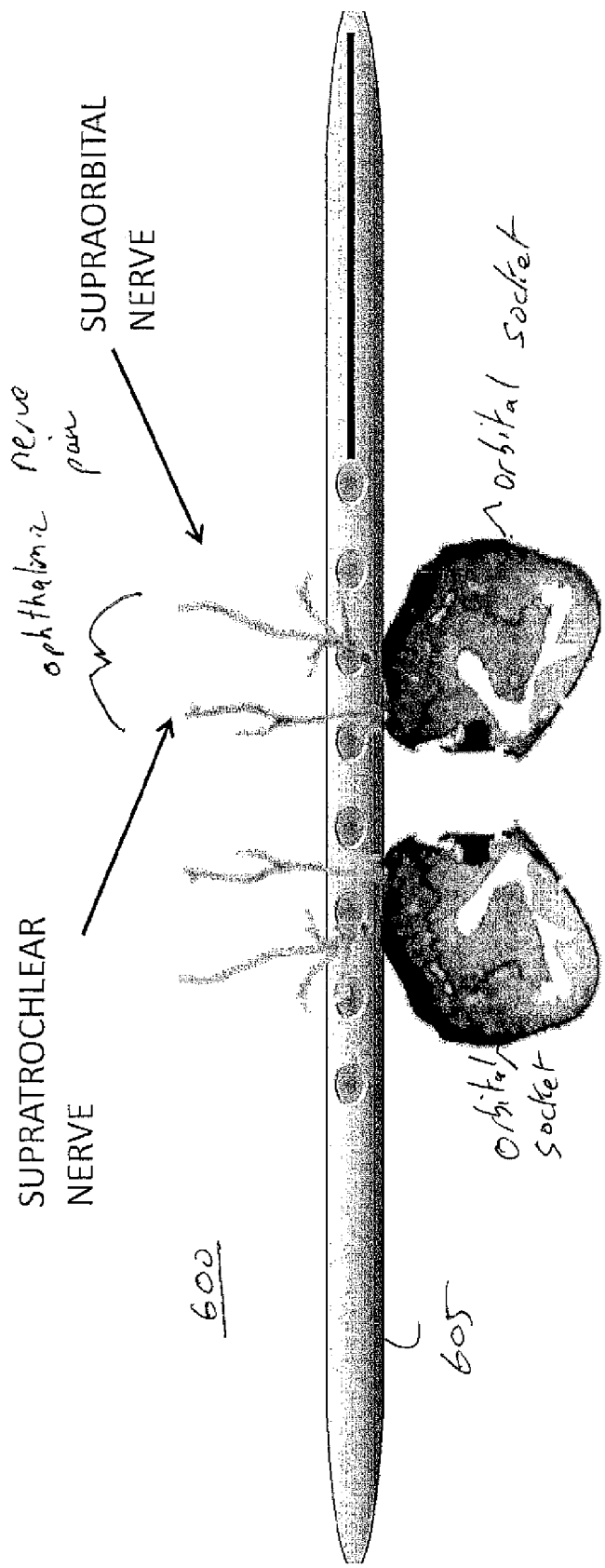
FIG. 6 illustrates an implanted electrode lead and its orientation with regard to the orbital sockets and the ophthalmic nerve pairs.
Figure 2:
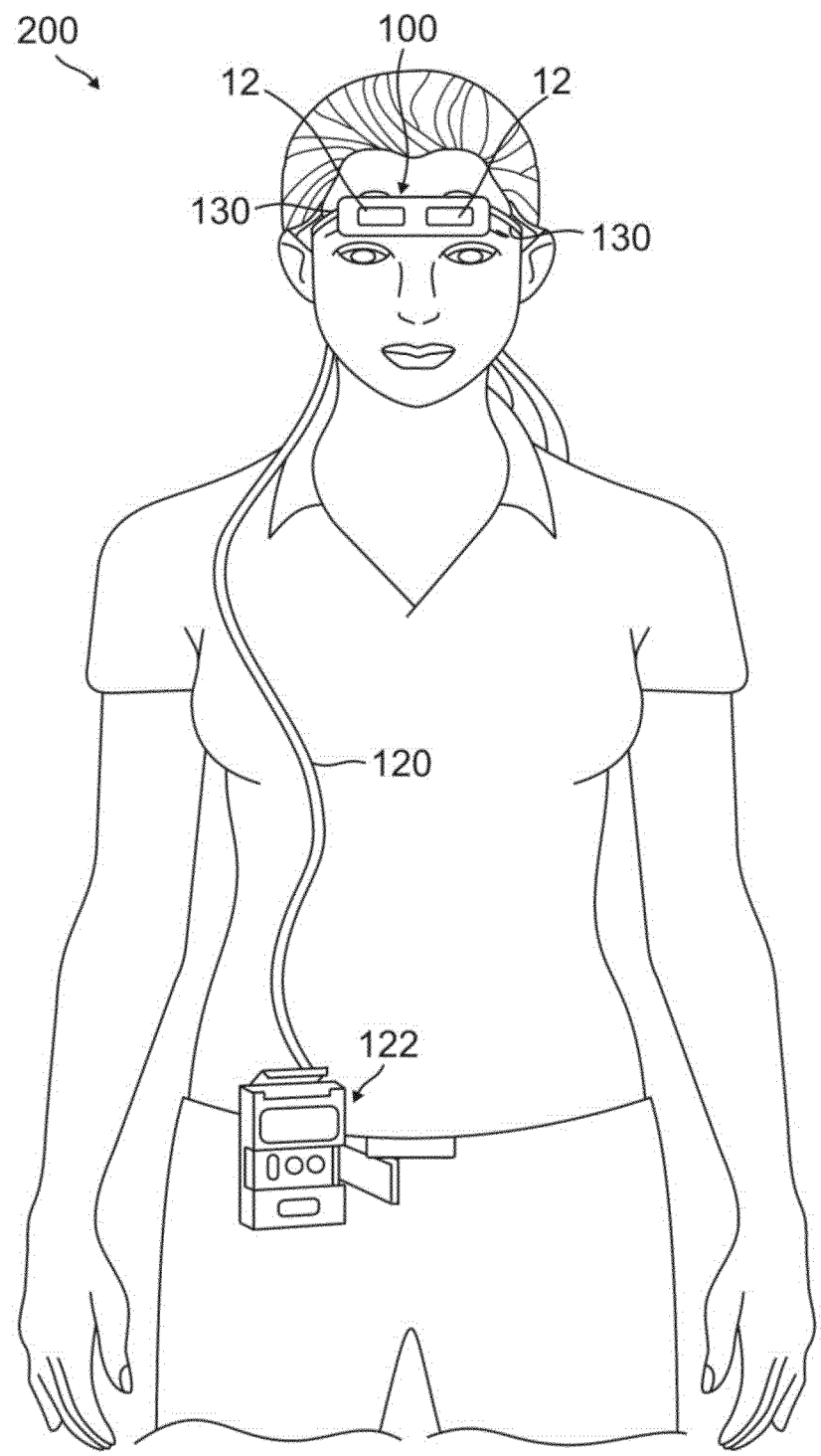
Figure 3A:
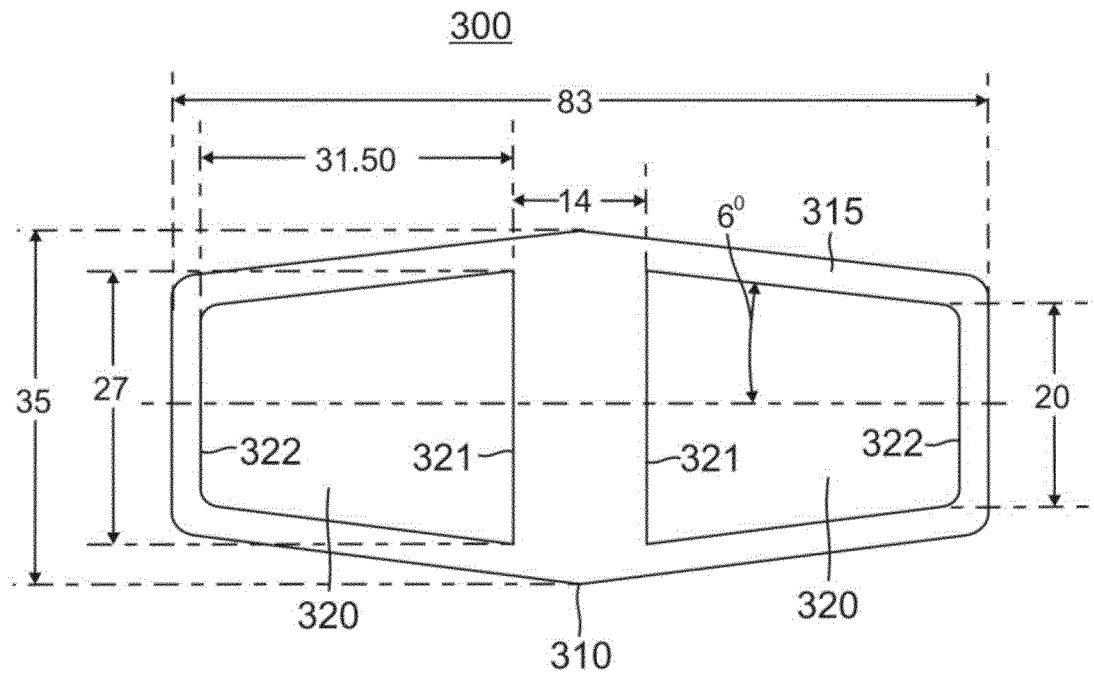
Figure 3B:
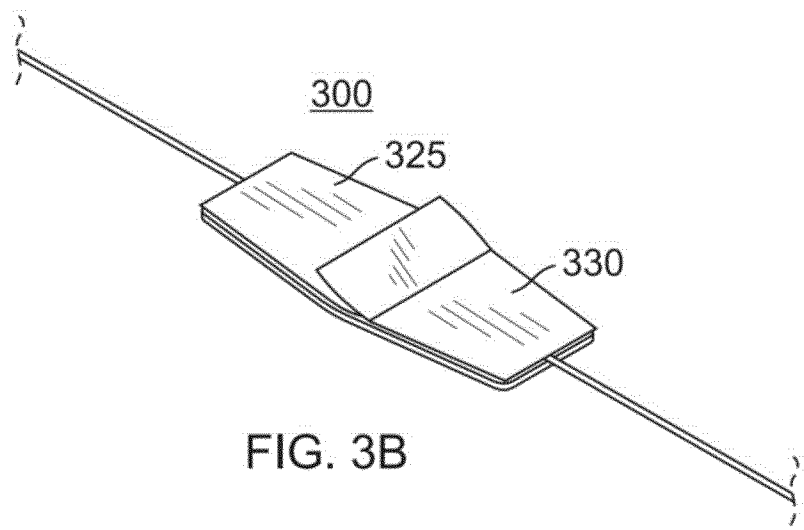

The subcutaneous electrode may comprise a round lead or a ribbon-shaped lead. An example subcutaneous electrode 600 is shown in FIG. 6. Subcutaneous electrode 600 comprises a ribbon-shaped body or lead 605 that includes two or more contacts 610. Lead 605 may be several millimeters wide and approximately 1 mm thick. Connecting wires that couple to lead 605 to provide electrical power to contacts 610 are not shown for illustration clarity. Advantageously, the ophthalmic nerve pair above each orbital socket innervates and is thus attached to the frontalis muscle (not illustrated). Thus, as the dissection tool (discussed further below) dissects across the forehead in the plane defined by the loose areolar tissue, the ophthalmic nerve pairs will safely displace with the frontalis and thus will not be subjected to any danger of severing by either dissection tool or the lead 605. But the ophthalmic nerve pairs will then be very close or adjacent to contacts 610 such that TNS may be therapeutically administered.

An example blunt dissection tool 700 is shown in a side-elevational view in FIG. 7A and a plan view in FIG. 7B. A proximal end of dissection tool 700 is removably attached to a distal end of lead 605. Like lead 605, dissection tool 700 may be substantially ribbon-shaped to facilitate dissection through the loose areolar connective tissue plane. A distal end of dissection tool 700 may be slightly curved to match the expected curvature of the forehead. Dissection tool 700 comprise steel or plastic that is semi-resilient so that a clinician can force it through the loose areolar connective tissue plane yet the dissection tool 700 will follow the curvature of the forehead. For example, dissection tool 700 may comprise surgical steel or plastic. If dissection tool 700 is not radiopaque, it may include radiopaque markers so that a clinician may properly position dissection tool 700 as it dissects the loose areolar connective tissue plane. Similarly, lead 605 may be radiopaque or include radiopaque markers.

In alternative embodiments, the dissection tool may be at least partially hollow so as to enclose a distal portion of a round electrode lead. Regardless of the shape of the dissection tool and the corresponding lead, the dissection tool includes a mechanism to selectively engage with and disengage from the lead. For example, the dissection tool may include a clasp resiliently grasps lead so as to engage the lead to the dissection tool. Such a dissection tool would include a wire connected to the clasp such that the clasp may be opened by pulling on the wire to disengage the lead from the dissection tool. It will be appreciated that numerous other mechanisms may be used to selectively engage and disengage the lead.

A method of implanting a lead using a dissection tool will now be discussed. A suitable insertion point is the hair line just anterior and proximal to the ear. For example, a large bore needle may be used to form the insertion point such that the large bore needle enters the loose areolar connective tissue plane at the insertion point. To aid the introduction of the distal end of the dissection tool into the loose areolar connective tissue plane (with the proximal end of the dissection tool being attached to the distal end of the lead), the needle may be angled anteriorly and advanced slightly into the loose areolar connective tissue. Dissection tool 700 may then be advanced through the needle into the loose areolar connective tissue space. Using imaging such as fluoroscopy, the clinician may continue to advance the dissection tool across the forehead above the eyebrows and adjacent the supraorbital and supratrochlear foramina (or notches). The loose areolar connective tissue has relatively little resistance as compared to the tougher frontalis muscle and the pericranium so a clinician may be assured that the dissection tool is following the loose areolar connective tissue space or plane by the amount of force necessary to continue the dissection. The distal end of the dissection tool should be sharp enough so as to readily dissect through the loose areolar connective tissue yet be sufficiently dull so as to resist dissecting into the frontalis muscle. Such a dissection is quite advantageous since the supraorbital and supratrochlear nerves pierce the underbelly of the frontalis muscle and will thus naturally displace away from the dissection tool with the frontalis muscle as the dissection tool pushes through the loose areolar connective tissue space. Once the lead is properly aligned with the ophthalmic nerve pairs such as shown in FIG. 6, a cut may be made to expose the distal end of the dissection tool. The dissection tool preferably has a longitudinal extent such that its distal end will be advanced past the hairline adjacent the opposite ear from the insertion point. The cut thus forms an extraction point to pull the dissection tool away from the lead after disengaging the lead from the dissection tool. With the lead properly positioned, it may also be secured to the skull using screws or other fasteners. Alternatively, the lead may be stitched to the subcutaneous fascia to secure it for subsequent TNS therapy. The lead may also be trimmed at this time at either its distal and/or proximal ends. Wires for driving the lead would extend from either the insertion or extraction point and couple to an external pulse generator. Alternatively, an internal pulse generator may be implanted with the lead.

With the lead implanted, the contacts may then be driven with current at the various operating parameters as discussed earlier. In this fashion, subcutaneous TNS may be used to treat the wide range of conditions as discussed earlier that involve ANS imbalance such as congestive heart failure, acute cardiac arrhythmias, ischemic heart disease, metabolic syndrome, Type 1 & 2 diabetes, Sjogren's syndrome, erectile dysfunction, ADHD, PTSD, and autoimmune disorders (e.g. rheumatoid arthritis, psoriatic arthritis, spondylitis, systemic lupus erythematosus, irritable bowel syndrome, Crohn's disease, ulcerative colitis, and inflammatory bowel disease). In addition, the subcutaneous implantation techniques and apparatus discussed herein may be used to provide TNS for treatment of a wide variety of neurological disorders, neuropsychiatric disorders, and medical disorders that do not involve ANS imbalances.

The above specification, examples and data provide a complete description of the structure and use of exemplary embodiments of the invention as claimed below. Although various embodiments of the invention as claimed have been described above with a certain degree of particularity, or with reference to one or more individual embodiments, those skilled in the art could make numerous alterations to the disclosed embodiments without departing from the spirit or scope of this invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

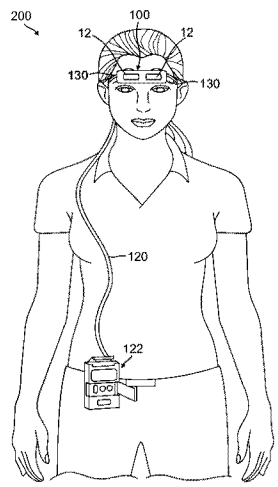

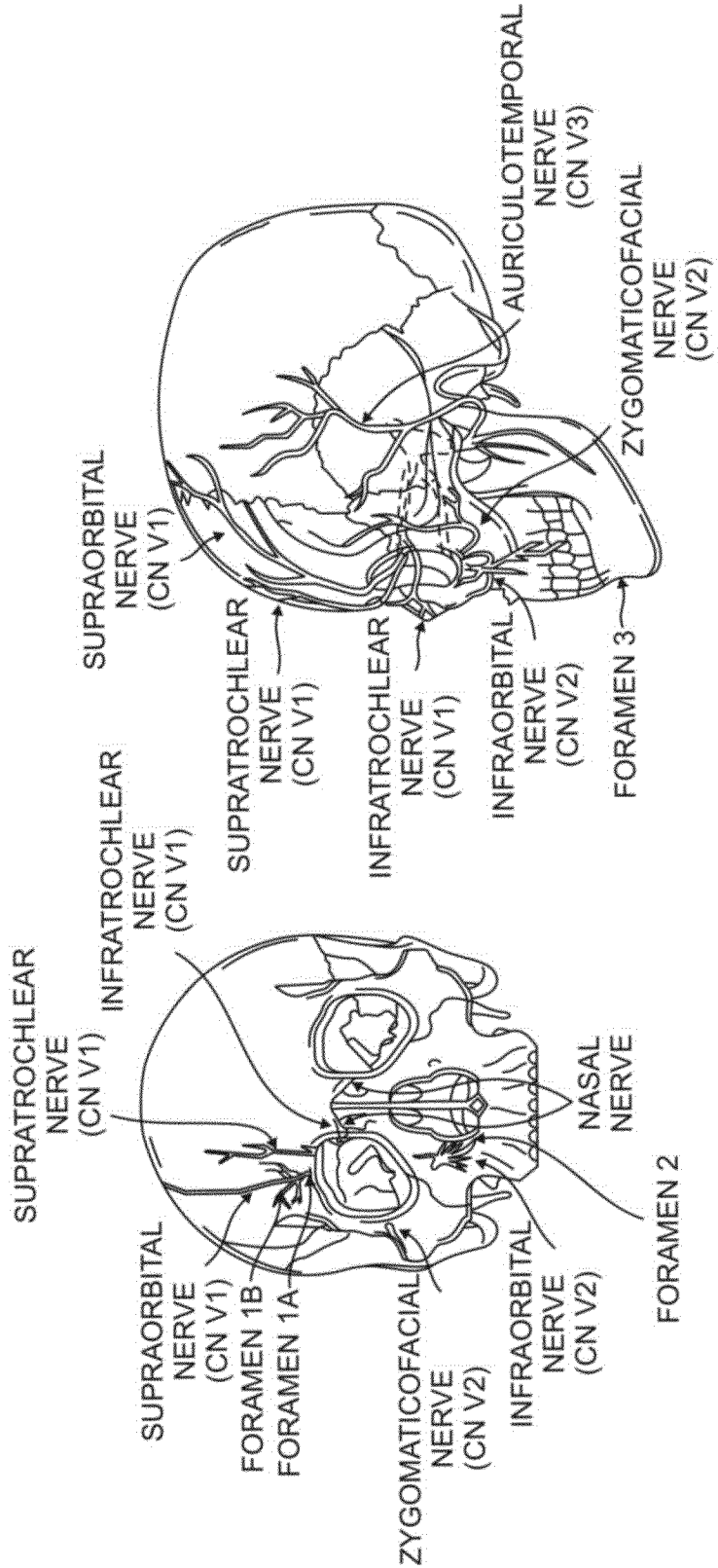

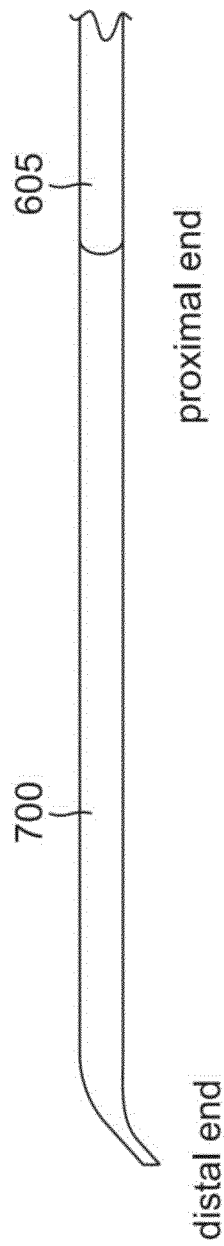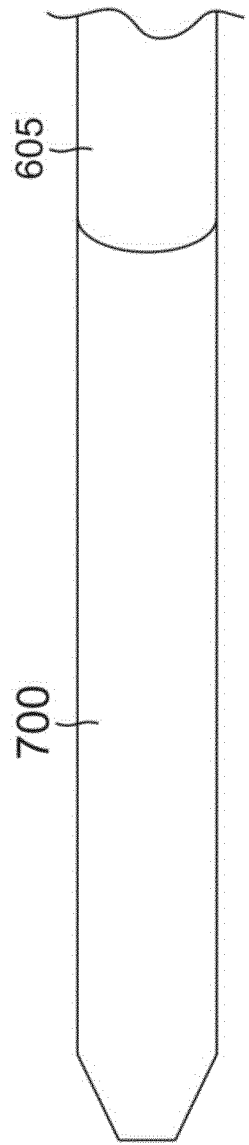

What is claimed is:

1. A method, comprising
applying a cutaneous electrode assembly to a patient's forehead; and
pulsing current through the electrode assembly to stimulate the supraorbital and supratrochlear nerves on the patient to increase a power spectral density for the patient's heart rate variability.

2. The method of claim 1, wherein the increased patient's heart rate variability is in a 0.1 to 0.15 Hz frequency band.

3. The method of claim 1, wherein the increased power spectral density is therapeutic for treatment of a disease selected from the group consisting of congestive heart failure, acute cardiac arrhythmias, ischemic heart disease, metabolic syndrome, Type 1 & 2 diabetes, Sjogren's syndrome, erectile dysfunction, ADHD, PTSD, rheumatoid arthritis, psoriatic arthritis, spondylitis, systemic lupus erythematosus, irritable bowel syndrome, Crohn's disease, ulcerative colitis, and inflammatory bowel disease.

4. The method of claim 1, wherein applying the cutaneous electrode assembly comprises aligning a midline of the cutaneous electrode assembly with the patient's nasal midline, and adhering the aligned cutaneous electrode assembly to the patient's forehead such that a first electrode contact overlays a first ophthalmic nerve pair on a first side of the patient's forehead and such that a second electrode contact overlays a second ophthalmic nerve pair on an opposing second side of the patient's forehead.

5. The method of claim 4, wherein the first electrode contact comprises a pair of electrode contacts configured to stimulate the first ophthalmic nerve pair in an afferent direction.

6. The method of claim 1, wherein the second electrode contact comprises a pair of electrode contacts configured to stimulate the second ophthalmic nerve pair in an afferent direction.

7. The method of claim 1, wherein pulsing the current comprises using a pulse amplitude between 50 µA and 20 mA, a pulse width between 50 µs and 500 µs, and a pulse frequency between 10 Hz and 300 Hz.

8. The method of claim 1, wherein pulsing the current comprises pulsing over duty cycle periods such that the current is pulsed in an on portion of each duty cycle period and not pulsing for a remaining off portion of each duty cycle period, and wherein a ratio of the on portion to the duty cycle period defines a duty cycle.

9. The method of claim 8, wherein pulsing the current comprises using a duty cycle between 5% and 100%.

10. The method of claim 8, wherein pulsing the current comprises using a duty cycle of 50% and a duty cycle period of 60 seconds.

11. A method, comprising:
implanting an electrode lead including a plurality of contacts into a patient such that a first one of the contacts is adjacent a first supraorbital nerve and such that a second one of the contacts is adjacent a second supraorbital nerve; and
pulsing current through the contacts to stimulate the supraorbital and supratrochlear nerves on the patient to increase a power spectral density for the patient's heart rate variability.

12. The method of claim 11, wherein the increased patient's heart rate variability is in a 0.1 to 0.15 Hz frequency band.

13. The method of claim 11, wherein the increased power spectral density is therapeutic for treatment of a disease selected from the group consisting of congestive heart failure, acute cardiac arrhythmias, ischemic heart disease, metabolic syndrome, Type 1 & 2 diabetes, Sjogren's syndrome, erectile dysfunction, ADHD, PTSD, rheumatoid arthritis, psoriatic arthritis, spondylitis, systemic lupus erythematosus, irritable bowel syndrome, Crohn's disease, ulcerative colitis, and inflammatory bowel disease.

14. The method of claim 11, further comprising:
engaging the electrode lead to a dissection tool, wherein implanting the electrode lead comprises driving the engaged dissection tool across the patient's loose areolar connective tissue.

15. The method of claim 11, wherein implanting the electrode lead further comprises introducing the engaged dissection tool through a cannula into the loose areolar connective tissue in the forehead.

16. An integrated electrode assembly, comprising:
a cutaneous electrode assembly including a first electrode contact configured to stimulate a first ophthalmic nerve pair on a first side of a patient's forehead and a second electrode contact configured to stimulate a second ophthalmic nerve pair on an opposing second side of the patient's forehead; and
a housing removably attached to the cutaneous electrode assembly, wherein the housing includes a pulse generator configured to generate electrical pulses at the first and the second electrodes for stimulation of the first and second ophthalmic nerve pairs to increase a power spectral density for the patient's heart rate variability and a power supply to power the pulse generator.

17. The integrated electrode assembly of claim 16, wherein the housing further comprises a wireless interface configured to wirelessly receive configuration parameters for the pulse generator.

18. The integrated electrode assembly of claim 16, wherein the housing further comprises a manually-actuated interface configured to receive manually-entered configuration parameters for the pulse generator.

* * * * *

UNITED STATES PATENT AND TRADEMARK OFFICE
CERTIFICATE OF CORRECTION

PATENT NO.         : 9,731,127 B2
APPLICATION NO.    : 14/907273
DATED              : August 15, 2017
INVENTOR(S)        : Colin Kealey and Leon Ekchian It is certified that error appears in the above-identified patent and that said Letters Patent is hereby corrected as shown below:

On the Title Page

Delete title page and substitute therefore attached new title page.

In the Drawings

Replace Sheet 1/8, Figs. 1A and 1B with the attached Replacement Sheet 1/8.

Replace Sheet 2/8, Fig. 2 with the attached Replacement Sheet 2/8.

Replace Sheet 3/8, Figs. 3A and 3B with the attached Replacement Sheet 3/8.

Figure 4A:
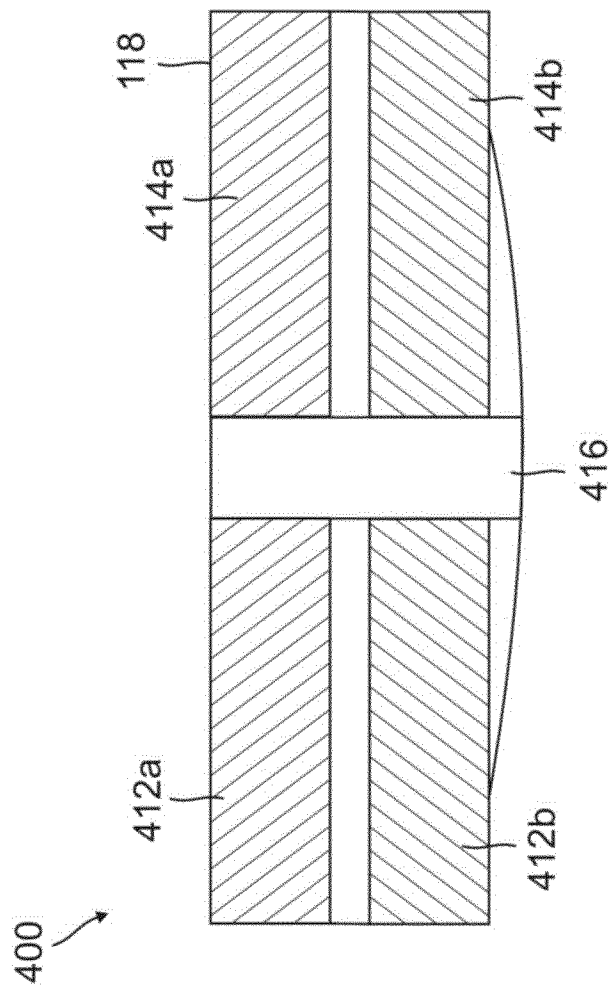
FIG. 4A is a plan view of a cutaneous electrode assembly including two pairs of contacts, wherein each pair of contacts is configured to stimulate a corresponding ophthalmic nerve pair.
Figure 4B:
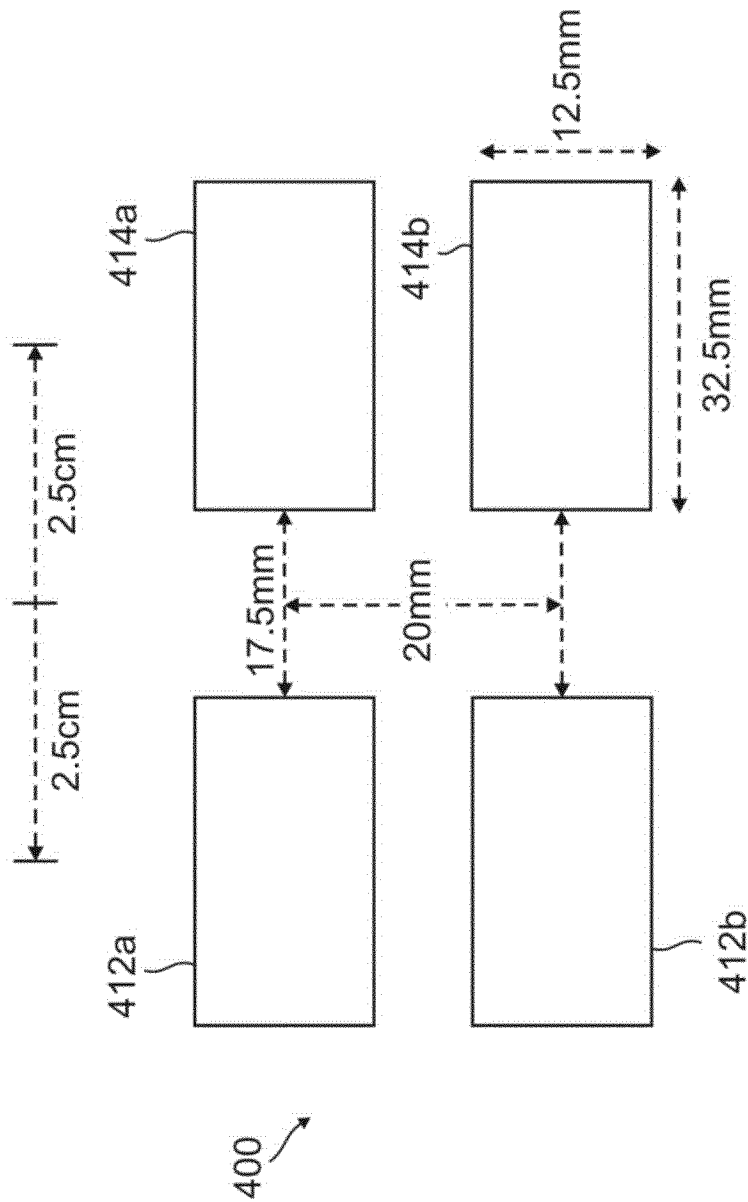

Replace Sheet 4/8, Fig. 4A with the attached Replacement Sheet 4/8.

Replace Sheet 5/8, Fig. 4B with the attached Replacement Sheet 5/8.

Replace Sheet 6/8, Fig. 5 with the attached Replacement Sheet 6/8.

Replace Sheet 7/8, Fig. 6 with the attached Replacement Sheet 7/8.

Replace Sheet 8/8, Figs. 7A and 7B with the attached Replacement Sheet 8/8.

Signed and Sealed this
Second Day of October, 2018

Andrei Iancu
*Director of the United States Patent and Trademark Office*

(12) United States Patent
Kealey et al.

(10) Patent No.: US 9,731,127 B2
(45) Date of Patent: Aug. 15, 2017

(54) MODULATION OF AUTONOMIC NERVOUS SYSTEM ACTIVITY AND INTEGRATED ELECTRODE ASSEMBLIES FOR TRIGEMINAL NEUROSTIMULATION

(71) Applicant: NeuroSigma, Inc., Los Angeles, CA (US)

(72) Inventors: Colin Kealey, Los Angeles, CA (US); Leon Ekchian, Los Angeles, CA (US)

(73) Assignee: NeuroSigma, Inc., Los Angeles, CA (US)

( * ) Notice: Subject to any disclaimer, the term of this patent is extended or adjusted under 35 U.S.C. 154(b) by 0 days.

(21) Appl. No.: 14/907,273

(22) PCT Filed: Apr. 24, 2014

(86) PCT No.: PCT/US2014/035347
§ 371 (c)(1),
(2) Date: Jan. 22, 2016

(87) PCT Pub. No.: WO2014/176450
PCT Pub. Date: Oct. 30, 2014

(65) Prior Publication Data
US 2016/0184585 A1    Jun. 30, 2016

Related U.S. Application Data

(60) Provisional application No. 61/815,718, filed on Apr. 24, 2013.

(51) Int. Cl.
*A61N 1/00*    (2006.01)
*A61N 1/36*    (2006.01)
(Continued)

(52) U.S. Cl.
CPC ....... *A61N 1/36025* (2013.01); *A61N 1/0456* (2013.01); *A61N 1/0551* (2013.01);
(Continued)

(58) Field of Classification Search
CPC .............. A61N 1/36025; A61N 1/0456; A61N 1/0551; A61N 1/36114; A61N 1/36053; A61N 1/0492
See application file for complete search history.

(56) References Cited

U.S. PATENT DOCUMENTS 6,358,201 B1    3/2002    Childre et al.
8,380,315 B2    2/2013    DeGiorgio et al.
(Continued)

FOREIGN PATENT DOCUMENTS

WO    WO 2012/075192    6/2012

OTHER PUBLICATIONS

International Search Report and Written Opinion, PCT/US2014/035347, Sep. 29, 2014, 11 pages.

*Primary Examiner* — Robert N Wieland
(74) *Attorney, Agent, or Firm* — Haynes and Boone, LLP

(57) ABSTRACT

Cutaneous and subcutaneous TNS embodiments are disclosed for addressing autonomic nervous system imbalances. A cutaneous electrode assembly is applied to a patient's forehead, and a current is pulsed through the electrode assembly to stimulate the supraorbital and supratrochlear nerves on the patient to increase activity for the patient's parasympathetic nervous system. Pulsing the current increases the power spectral density for the patient's heart rate variability in a 0.1 to 0.15 Hz frequency band.

18 Claims, 8 Drawing Sheets